United States Patent [19]

Skwor et al.

[11] Patent Number: 5,042,464
[45] Date of Patent: Aug. 27, 1991

[54] OFF-THE SHELF CUSTOM KNEE BRACE

[75] Inventors: Edward P. Skwor, Savage, Minn.; Timothy C. Sandvig, Woodville, Wis.; Franklin S. Lange, Golden Valley, Minn.

[73] Assignee: Minnesota Mining and Manufacturing Company, St. Paul, Minn.

[21] Appl. No.: 612,411

[22] Filed: Nov. 13, 1990

Related U.S. Application Data

[63] Continuation-in-part of Ser. No. 93,408, Sep. 4, 1987, Pat. No. 5,002,047, which is a continuation-in-part of Ser. No. 903,281, Sep. 3, 1986, Pat. No. 4,968,542, and a continuation-in-part of Ser. No. 15,972, Feb. 18, 1987, Pat. No. 4,946,726, which is a continuation-in-part of Ser. No. 784,345, Oct. 4, 1985, Pat. No. 4,683,877.

[51] Int. Cl.$^5$ .............................. A61F 3/00; A61F 5/04
[52] U.S. Cl. ................................ 128/80 C; 128/89 R; 128/90
[58] Field of Search ............... 128/90, 89 R, 91 R, 128/80 R, 80 B, 80 F, 16 S, 87 R, 84 R, 80 H, 80 D, 80 C, 166, 252, 599

[56] References Cited

U.S. PATENT DOCUMENTS

| | | | |
|---|---|---|---|
| 3,798,799 | 3/1974 | Hanson et al. | 36/2.5 AL |
| 3,882,561 | 5/1975 | Hanson et al. | 12/142 |
| 3,942,522 | 3/1976 | Kinnier Wilson | 128/90 |
| 4,083,127 | 4/1978 | Hanson | 36/93 |
| 4,144,658 | 3/1979 | Swan, Jr. | 36/117 |
| 4,182,056 | 1/1980 | Dalebout | 36/117 |
| 4,233,967 | 11/1980 | Daniell, Jr. | 128/90 |
| 4,255,202 | 3/1981 | Swan, Jr. | 106/122 |
| 4,301,564 | 11/1981 | Dalebout | 12/146 |
| 4,347,213 | 8/1982 | Rogers, Jr. | 264/510 |
| 4,751,920 | 6/1988 | Mauldin | 128/80 F |
| 4,928,670 | 5/1990 | Delorenzo | 128/89 R |
| 4,928,678 | 5/1990 | Grim | 128/90 |
| 4,953,543 | 9/1990 | Grim | 128/80 F |
| 4,961,416 | 10/1990 | Moore | 128/80 F |

Primary Examiner—Danton D. DeMille
Assistant Examiner—Michael Brown
Attorney, Agent, or Firm—Gary L. Griswold; Walter N. Kirn; Charles D. Levine

[57] ABSTRACT

An orthotic knee brace is custom fit to the user's leg without requiring any separate casting steps. The brace includes a thigh cuff which is hinged to a calf cuff. Straps can provide support to at least a portion of the leg. A pad is removably disposed on the interior surface of both the thigh cuff and the calf cuff and contacts the user's leg. The pad is initially pliable when placed around the user's leg and conforms to the leg shape. After a predetermined time the pad cures to maintain the leg shape even after the brace is removed.

13 Claims, 4 Drawing Sheets

OFF-THE SHELF CUSTOM KNEE BRACE

CROSS-REFERENCE TO RELATED APPLICATIONS

This application is a continuation-in-part of Ser. No. 93,408 filed Sept. 4, 1987 which issued as U.S. Pat. No. 5,002,047 on Mar. 26, 1991 for "Orthotic Pads and Methods," which in turn is a continuation-in-part of the following U.S. patent applications: Ser. No. 903,281 filed Sept. 3, 1986 which issued as U.S. Pat. No. 4,9068,542 on Nov. 6, 1990 for "Curable Material for Semi-rigid Resilient Orthopedic Support" and Ser. No. 15,972 filed Feb. 18, 1987 which issued as U.S. Pat. No. 4,946,726 on Aug. 7, 1990 for "Orthopedic Splinting Articles and Methods" which is a continuation-in-part of Ser. No. 784,345 filed Oct. 4, 1985 which issued as U.S. Pat. No. 4,683,877 on Aug. 4, 1987 for "Orthopedic Casting Article and Method."

TECHNICAL FIELD

The present invention relates to orthotic knee braces. More particularly, the present invention relates to orthotic knee braces that can be fitted.

BACKGROUND OF THE INVENTION

Many diverse articles such as medical devices, orthotic devices, clothing and sports equipment, and furniture have incorporated elements which tend to conform to the shape of the user or some part of the user. Air splints are inflated to conform to the limb of an injured user, but are not intended to be reused in the conformed state. The splint is deflated and reinflated for reuse around another limb.

In U.S. Pat. No. 4,347,213 to Rogers, Jrs., cushions for chairs and other seats are made to conform to human body parts. In this device, a complex series of steps is required to conform the cushion to the contours of a particular body as follows. First, a sealed pliable bag filled with polystyrene pellets is placed in contact with the body and then a vacuum is applied to the bag to solidify the polystyrene mass. X-rays are used to confirm proper positioning. Next, plaster is applied to the external surface of the bag to form a shell, the bag and polystyrene are removed, and the shell serves as a mold for polyurethane which will serve as the cushion after it is covered. Alternatively, the polystyrene mass is smoothed with appropriate material, rigidified, and coated with a high friction surface.

Ski boot internal liners, such as disclosed in U.S. Pat. No. 4,083,127 to Hanson, and U.S. Pat. Nos. 4,144,658 and 4,255,202 to Swan, Jr. are further examples of products which conform to human body parts. These ski boot liners are flow pads which conform to the foot of a user. However, none of these liners are permanently formed to a specific foot by contacting the device with the foot. In these devices, the formable liner is designed to contour to the foot inside the boot at a particular time and to later resume the original uncontoured state when not in use.

Foot orthotics, such as disclosed in Ser. No. 93,408 filed Sept. 4, 1987 for "Orthotic Pads and Methods," assigned to the assignee of this invention, are molded to a specific foot and retain that shape permanently. However, as discussed in that patent, the use of a resin impregnated foam requires that a removable protective barrier be used between the actual orthotic device and the user's foot to prevent contact between the skin and the resin.

Known custom fit orthotic knee braces are deficient in that while substantially precisely fitting the leg of a particular user, they must be fitted using a series of steps and must be made in a shop. They can not be made in the presence of the potential user while the user waits. Custom fit braces typically require that a mold of the user's leg be made, and the mold serve as a form for a plaster of paris mixture which models the user's leg. The brace is then manufactured from the leg model. This process requires at least several days and can take several weeks between the initial fitting and the day the user takes home the brace. Additionally, the use of several steps to shape the brace reduces the precision of the brace. The resulting brace is not as precise as if it were shaped directly on the user's leg.

SUMMARY OF THE INVENTION

The orthotic knee brace of the present invention overcomes the disadvantages of the known custom fit braces by being custom fit to the user's leg without requiring any separate casting or leg measuring steps. The brace includes a thigh cuff for fitting around the user's thigh and a calf cuff for fitting around the user's calf. Preferably, the thigh and calf cuffs extend for at least 180° around the thigh and calf, respectively, to provide sufficient leg support. First and second rigid thigh bars extend from the thigh cuff at opposite sides of the thigh cuff and first and second rigid calf bars extend from the calf cuff at opposite sides of the calf cuff. A first hinge connects the first thigh bar and the first calf bar and a second hinge connects the second thigh bar and the second calf bar. The hinges thereby connect the thigh cuff to the calf cuff. Additionally, the brace typically includes straps or other devices which provide support to at least a portion of the leg.

A pad is removably disposed on the interior surface of both the thigh cuff and the calf cuff and contacts the user's leg. The pad is initially pliable when placed around the user's leg and deforms to conform to the shape of the user's leg. After a predetermined time the pad cures to maintain permanently the shape of the user's leg even after the brace is removed from the user's leg, while remaining resilient. This permits the brace to be custom fit to the user's leg. The pad includes an open-celled foam impregnated with a resin system enclosed in a sleeve. The sleeve permits the pad to be molded to the user's leg without protective gear and without using any additional material layer between the user's leg and the brace. Additionally, the sleeve is made of a material which does not irritate the leg when the brace is fitted or when the brace is worn. This obviates the need for an undersleeve to be worn on the leg under the brace. The use of this type of pad enables the brace to be sized, molded, fit, and dispensed in a few hours such that the brace is both custom fit to the user's leg and purchased off-the-shelf.

DETAILED DESCRIPTION OF PREFERRED EMBODIMENTS

The orthotic knee brace of the present invention overcomes the disadvantages of the known custom fit braces by being custom fit to the user's leg without requiring any separate casting or leg measuring steps. The brace can be sized, molded, fit, and dispensed in a few hours and preferably less than an hour such that the brace is both custom fit to the user's leg and purchased off-the-shelf. By forming the brace directly around the user's leg, the precision of the brace's contours are improved over custom braces made by multi-step molding methods. Additionally, the brace provides a better fit than prior off-the-shelf braces. Moreover, the brace has improved repositionability in that when used and fitted on the leg by the user, because the brace precisely contours to the leg, the chances of improper placement on the leg and subsequent injury are greatly diminished as misplacement results in an uncomfortable and therefore noticeably improper fit.

The brace 10, shown in FIGS. 1-5, can provide prophylactic, post-operative, rehabilitation, or functional support to the leg of a user, and includes a rigid thigh cuff 12 for fitting around the user's thigh and a rigid calf cuff 14 for fitting around the user's calf. Preferably, the thigh and calf cuffs 12, 14 extend for at least 180° around the thigh and calf, respectively, encompassing the entire anterior portions of the leg to provide sufficient leg support.

Figure 1:
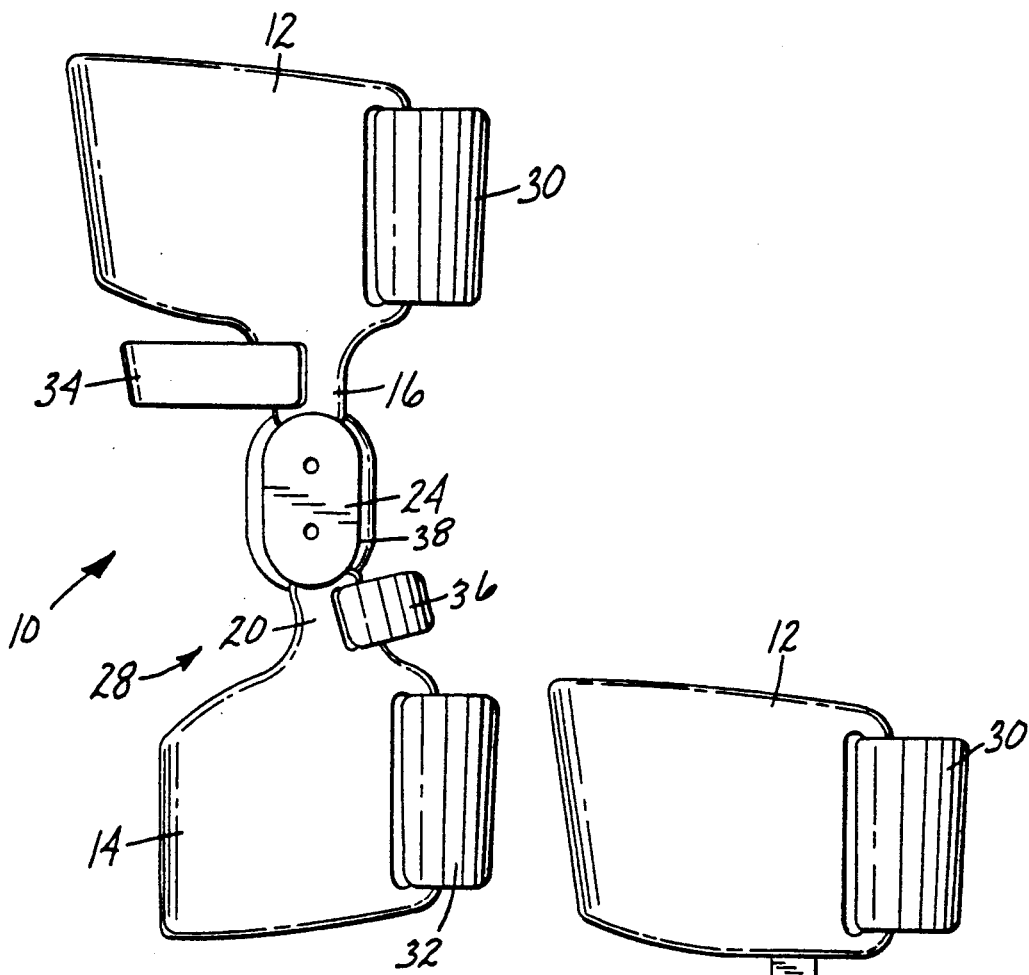
FIG. 1 is a side view of the orthotic knee brace according to one embodiment of the present invention.
Figure 2:
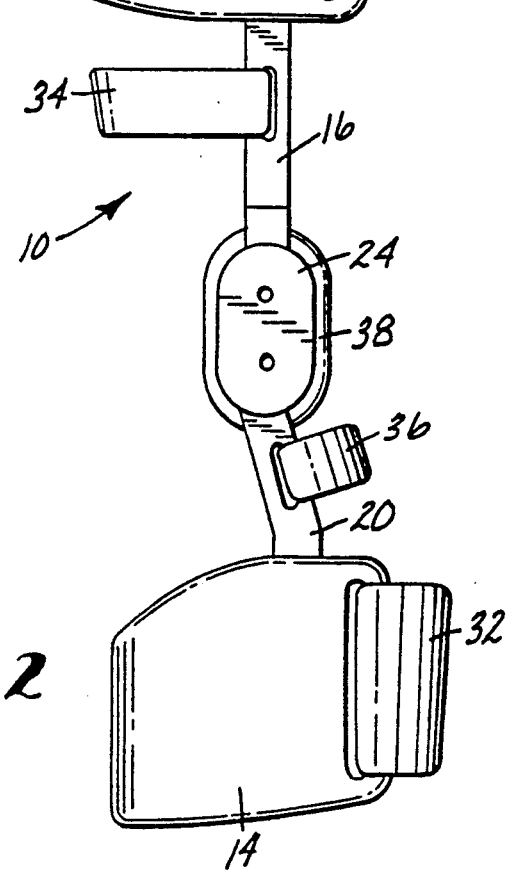
FIG. 2 is a side view of another embodiment of the knee brace.
Figure 3:
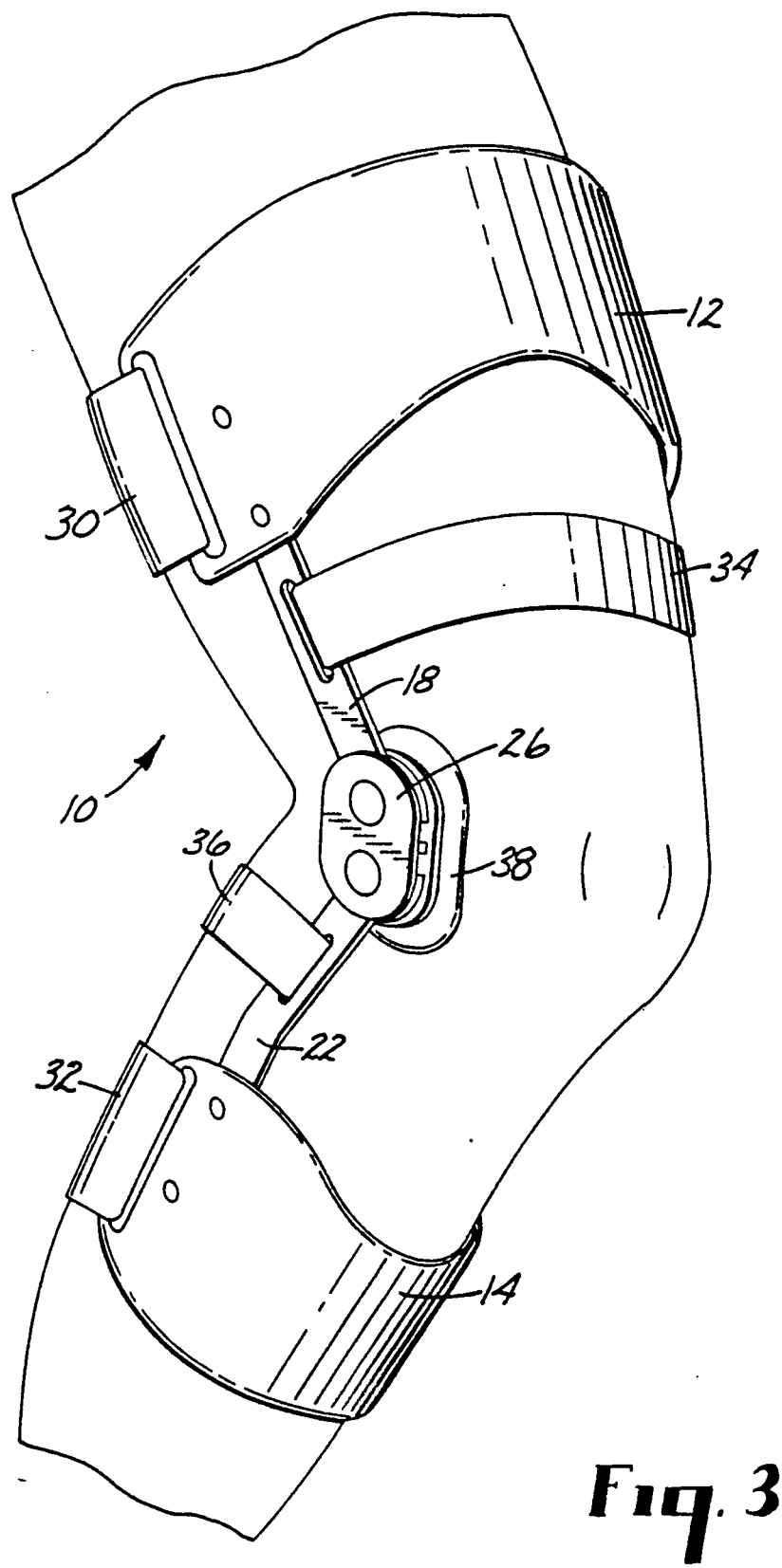
FIG. 3 is a perspective view of the knee brace of FIG. 1.

First and second rigid thigh bars 16, 18 extend from the thigh cuff 12 at opposite sides of the thigh cuff 12 and first and second rigid calf bars 20, 22 extend from the calf cuff 14 at opposite sides of the calf cuff 14. The thigh and calf bars 16, 18, 20, 22 can be formed as one piece with the respective thigh and calf cuffs 12, 14 as shown in FIG. 1, or can be formed separately and bolted, either rigidly or movably, to the respective thigh and calf cuffs 12, 14 as shown in FIG. 2. The thigh and calf bars 16, 18, 20, 22 extend along the medial and lateral sides of the leg as shown in FIG. 3. A first hinge 24 connects the first thigh bar 16 and the first calf bar 20 and a second hinge 26 connects the second thigh bar 18 and the second calf bar 22. The hinges 24, 26 thereby connect the thigh cuff 12 to the calf cuff 14 and can be any type of hinge including single or multiple axis hinges, or sliding hinges. The thigh and calf cuffs 12, 14, the thigh bars 16, 18, the calf bars 20, 22, and the first and second hinges 24, 26 combine to form the brace shell 28.

A posterior thigh strap 30 secures the thigh cuff 12 around the user's thigh and a posterior calf strap 32 secures the calf cuff 14 around the user's calf. Also, as best shown in FIGS. 1-3, the brace 10 typically includes additional straps or other devices which provide support to at least a portion of the leg. Any combination of anterior thigh or calf straps, posterior thigh or calf straps, or patella, hyperextension, or derotation straps can be used, depending on the specific portion of the leg to be supported or strengthened. In the illustrated brace 10, an anterior supra patella strap 34 and a posterior infra patella strap 36 are shown. Additionally, one or more condyle pads 38 can be positioned at or near the hinge 24, 26 locations between the thigh bars 16, 18 and calf bars 20, 22 adjacent the knee joint.

Figure 4:
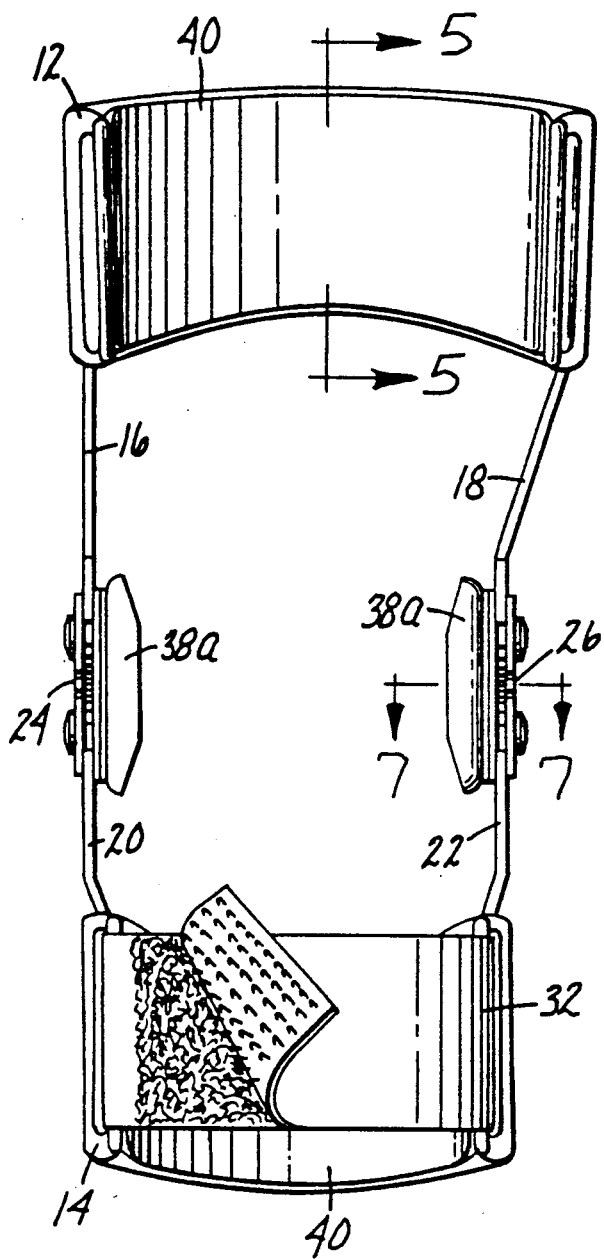
FIG. 4 is a rear view of the knee brace of FIG. 2 with parts shown in cross section.

Orthotic pads 40 are placed in the thigh and calf cuffs 12, 14 to custom fit the brace 10 to the leg, as described below. These pads 40, combined with the thigh and calf cuffs 12, 14 extending around most of the leg circumference, obviate the need for the posterior thigh and calf straps 30, 32 to encircle the leg, as shown in FIG. 4 with respect to the calf strap 32. The straps 30, 32 are not needed to fit the brace 10 to the leg. Rather, the straps 30, 32 only secure the brace 10 to the leg.

Figure 7:
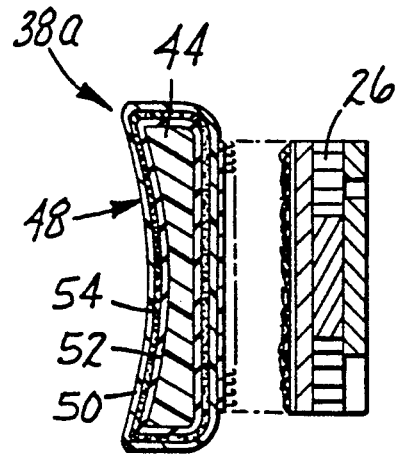
FIG. 7 is a cross-sectional view of the orthotic condyle pad used in the brace of FIG. 4.

An orthotic pad 40 is removably disposed on the interior surface of both the thigh cuff 12 and the calf cuff 14 as by hook and loop fasteners 42 and contacts the user's leg. The pad 40 is resilient and provides adjustability in fitting the brace 10 to the leg of the user. Additionally, an orthotic pad 40 can be shaped for use as the condyle pad 38a, as shown in FIGS. 4 and 7. The pad 40 is initially pliable when placed around the user's leg and deforms to conform to the shape of the user's leg. After a predetermined time the pad 40 cures to maintain precisely and permanently the shape of the user's leg even after the brace 10 is removed from the user's leg, while remaining resilient. This permits the brace 10 to be custom fit to the user's leg.

The orthotic pad 40 preferably includes a resin-impregnated foam sheet as described in Ser. No. 93,408 filed Sept. 4, 1987 for "Orthotic Pads and Methods." That application is a continuation-in-part of the following United States applications: Ser. No. 903,281, filed Sept. 3, 1986 for "Curable Material for Semi-rigid Resilient Orthopedic Support" and Ser. No. 15,972, filed Feb. 18, 1987 for "Orthopedic Splinting Articles and Methods," now U.S. Pat. No. 4,946,726 (which is a continuation-in-part of Ser. No. 784,345, filed Oct. 4, 1985 for "Orthopedic Casting Article and Method"). The disclosure of all of these applications is incorporated by reference.

Figure 5:
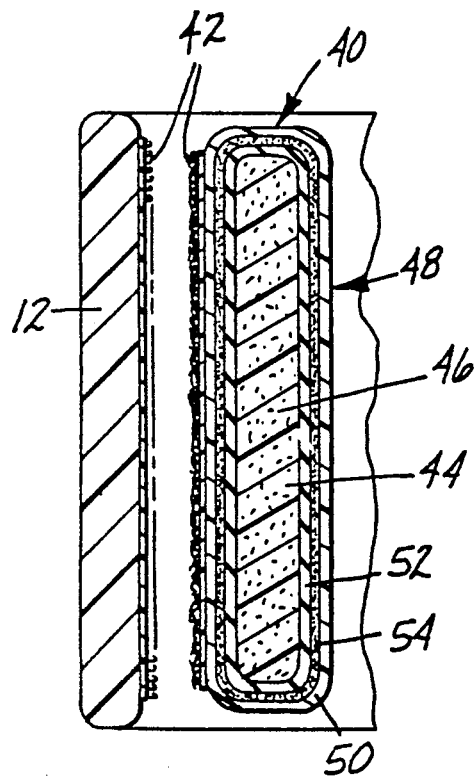
FIG. 5 is a cross-sectional view of the knee brace taken along line 5—5 of FIG. 4.
Figure 6:
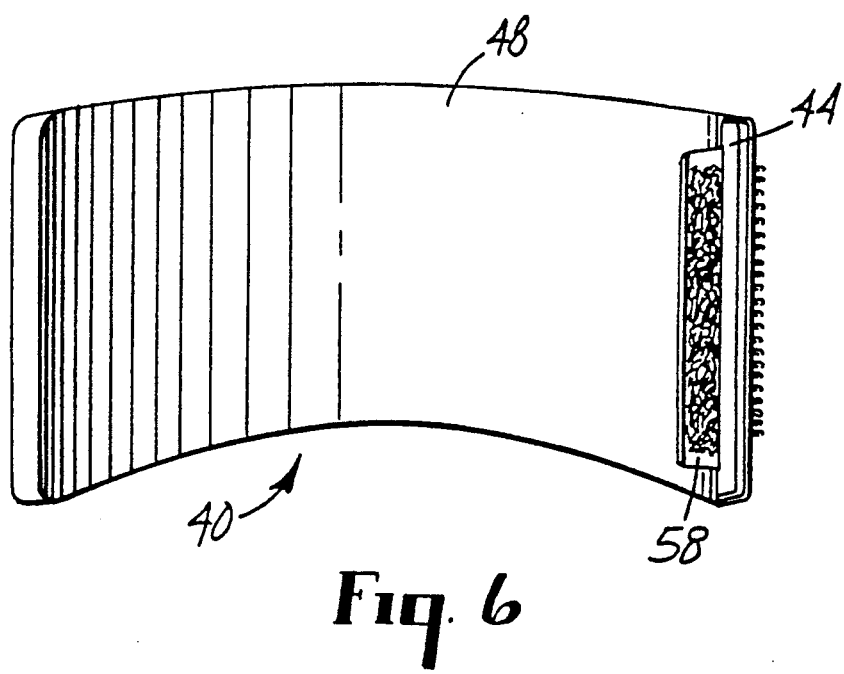
FIG. 6 is perspective view of the orthotic pad used in the braces of FIGS. 1-5.

Referring to FIGS. 5, 6, and 7, the orthotic pad 40 includes a conformable, pliable, curable foam sheet 44. Preferably, the pad 40 is an open-celled foraminous structure with interconnecting cells or cavities caused by a sufficient number of the wall membranes of the foam cells having been removed and has a density in the range of about 0.02 to about 0.15 g/cm$^3$. The open-celled foam sheet 44 is impregnated with a resin system 46 which intermingles with and surrounds the wall membranes of the cells. The resin system 46 includes a resin and any other ingredients, such as catalysts, stabilizers, plasticizers, or antioxidants, which are added to the resin or its components, prior to or simultaneously with their impregnation into the foam sheet 44. The preferred resins for impregnating the foam sheet 44 are water-curable, isocyanate functional, polyurethane prepolymers prepared by the reaction of a polyol with an excess of a polyisocyanate. The foam sheet 44 can be any one of a number of extensible foams that are open-celled, such as polyether- or polyester-based polyurethane foams as long as it can be resin-loaded sufficiently to provide a satisfactory orthotic pad. The foam sheets can frequently be impregnated in a solventless manner, to avoid prolonged contact of residual traces of solvent with the body part.

Before the pad 40 is placed on the cuffs 12, 14 and the brace 10 is mounted around the user's leg, the resin is activated by a curing agent. Preferably the resin cures when contacted with water. Thus, the resin can be activated generally by spraying or immersing the pad in water. To produce suitable pads, a set time of less than about 20 minutes, and preferably 10 minutes following activation of the resin is preferred. The set time is the time needed for an activated blank to hold its conformed shape; at this time it could be removed from contact with the body part while it continues to cure. Curing refers to the resin cross-linking to the furthest extent under the chosen conditions. Curing a resin impregnated foam pad is the preferred way of producing a pad that has captured and will hold the shape of the limb.

The pad 40 can be prepared and packaged having dimensions intended for use in apposition to a particular type and/or size of leg. Generally, the most important dimension will be its thickness, the distance between the major surface to be contacted with the leg, and the opposite surface.

The pad 40 also includes a sleeve 48 wrapped around the open-celled foam 44 impregnated with the resin system 46. The sleeve includes a flame-bonded nylon outer layer 50 which is made of a material which does not irritate the leg when the brace 10 is fitted or when the brace 10 is worn. This obviates the need for an undersleeve to be worn on the leg under the brace 10. A neoprene inner layer 52 acts as a moisture barrier and is adhered to the foam 44 after curing by an adhesive layer 54. The inner layer 52 of the sleeve 48 permits the pad 40 to be molded to the user's leg without protective gear such as gloves and without using any additional material layer between the user's leg and the brace 10. As shown in FIG. 6, the sleeve 48 can have a closable opening 56, including a flap 58 and hook and loop fasteners, which permits the foam sheet 44 to be inserted into the sleeve 48. The sleeve 48 is durable and water resistant, and can be provided in many colors.

A method of making the orthotic knee brace 10 includes selecting a thigh cuff 12 and a calf cuff 14 each having a desired general size for fitting around the user's thigh and calf, respectively. The general size of the thigh cuff 12 and the calf cuff 14 can be selected from one of three or four general sizes as determined from an initial measurement of the leg. The thigh cuff 12 is hingably connected to the calf cuff 14. This is accomplished by connecting first and second rigid thigh bars 16, 18 to the thigh cuff 12 at opposite sides of the thigh cuff 12, and connecting first and second rigid calf bars 20, 22 to the calf cuff 14 at opposite sides of the calf cuff 14. The first hinge 24 is connected to the first thigh bar 16 and the first calf bar 20, and the second hinge 26 is connected to the second thigh bar 18 and the second calf bar 22. The thigh cuff 12 and the calf cuff 14 can be connected individually for each brace 10 or can be preconnected so that the shell 28 is already assembled. Support devices are then mounted on the assembled brace shell to any of the thigh bars 16, 18, calf bars 20, 22, the thigh cuff 12, or the calf cuff 14.

Generally, pads 40 having different thicknesses (the distance between the major surfaces of the pad) and shapes can be used. Properly sized pads 40 are selected and removably disposed on the interior surface of both the thigh cuff 12 and the calf cuff 14 for contacting the user's leg.

The brace 10 is then custom fit to the user's leg as follows. The impregnated foam pad 40 is first removed from its water vapor-impermeable pouch just prior to application. The pad 40 is preferably used by activating the prepolymer resin by exposing the pad 40 to water such as by dipping or spraying to initiate setting and curing of the resin, and, if necessary, manually squeezing out excess water. Next, the pad 40 is mounted on the brace 10 and the brace 10 is properly positioned on the user's leg to deform the pad 40 to conform the pad to the shape of the user's leg. Because the resin-impregnated sheet 44 is enclosed within a neoprene sleeve 48, there is no need to place a flexible stockinet or other interface material between the user's skin and the brace 10 to prevent undesirable adhesion or contact between the brace 10 and leg.

The pad 40 has excellent compression moldability and conformability to provide a good fit to the shape of the subject's leg. The leg is kept in place as the resin sets, with sufficient pressure to cause the surface of the pad 40 to conform to the shape of the leg. The cured pad 40 bears an impression of the leg. It conforms closely and permanently to the shape and position of those parts of the leg held in apposition to the pad 40 during curing, even after the brace 10 is removed from the user's leg. The pad 40 also provides proper weight-bearing strength and cushioning properties.

In an alternative embodiment, the pad 40 can include a thermoformable foam which becomes pliable when heated to a temperature above its softening point. One usable thermoformable foam is available from ALIMED Inc. of Dedham, Mass., U.S.A. under the name Plastazote. In use, the thermoformable foam is heated until it is pliable, mounted on the shell 28, and then is placed around the user's leg. As the thermoformable foam cools, it hardens, causing the pad 40 to conform to the shape of the user's leg. Although the use of thermoformable foams is neater than resin impregnated foams, the thermoformable foams are not permanently hardened and may subsequently become pliable when subject to heat.

Numerous characteristics, advantages, and embodiments of the invention have been described in detail in the foregoing description with reference to the accompanying drawings. However, the disclosure is illustrative only and the invention is not intended to be limited to the precise embodiments illustrated. Various changes and modifications may be effected therein by one skilled in the art without departing from the scope or spirit of the invention. For example, the pad 40 can be made of other materials which are pliable when fitted around a user's leg and which permanently harden in a custom shape. Additionally, the orthotic knee brace can be used in veterinary settings for various orthopedic indications in animals such as equine angular limb deformities.

We claim:

1. An orthotic knee brace for providing support to the leg of a user, wherein the brace can be custom fit to the user's leg without requiring any separate casting or leg measuring steps, the brace comprising:

a thigh cuff for fitting around the user's thigh;

a calf cuff for fitting around the user's calf;

means for hingably connecting the thigh cuff to the calf cuff;

means for providing support to at least a portion of the leg; and a pad removably disposed on the interior surface of both the thigh cuff and the calf cuff which contacts the user's leg, wherein at least one of the pads is pliable when placed around the user's leg and then deforms to conform to the shape of the user's leg, and after a predetermined time hardens while remaining resilient to maintain permanently the shape of the user's leg even after the brace is removed from the user's leg, thereby permitting the brace to be custom fit to the user's leg.

2. The orthotic knee brace of claim 1 wherein the connecting means comprises:

first and second rigid thigh bars extending from the thigh cuff at opposite sides of the thigh cuff;

first and second rigid calf bars extending from the calf cuff at opposite sides of the calf cuff;

a first hinge connecting the first thigh bar and the first calf bar; and a second hinge connecting the second thigh bar and the second calf bar.

3. The orthotic knee brace of claim 1 wherein the thigh and calf cuffs extend for at least 180° around the leg.

4. The orthotic knee brace of claim 1 wherein the brace is both custom fit to the user's leg and provided off-the-shelf.

5. The orthotic knee brace of claim 1 wherein the pliable pad that deforms and hardens while remaining resilient comprises an open-celled foam impregnated with a resin system enclosed in a sleeve, wherein the sleeve permits the pad to be molded to the user's leg without protective gear and without using any additional material layer between the user's leg and the brace.

6. The orthotic knee brace of claim 5 wherein the resin system comprises a water-curable prepolymer resin including an isocyanate component and a polyol component and a catalyst capable of setting and curing the prepolymer resin upon exposure to water.

7. The orthotic knee brace of claim 5 wherein the sleeve is made of a material which does not irritate the leg when the brace is fitted or when the brace is worn thereby obviating the need for an undersleeve to be worn on the leg under the brace.

8. A method of making an orthotic knee brace, wherein the brace can be custom fit to the user's leg without requiring any separate casting or leg modeling steps, the method comprising the steps of:

selecting a thigh cuff having a desired general size for fitting around the user's thigh;

selecting a calf cuff having a desired general size for fitting around the user's calf;

hingably connecting the thigh cuff to the calf cuff;

selecting and mounting support devices to at least one of the thigh cuff, or the calf cuff;

selecting a properly sized pad for removably disposing on the interior surface of both the thigh cuff and the calf cuff and for contacting the user's leg;

mounting the pad in the respective thigh and calf cuffs;

mounting the brace mon the user's leg thereby deforming the pad to conform to the shape of the user's leg; and permitting at least one of the pads to harden while remaining resilient after a predetermined time to maintain permanently the shape of the user's leg even after the brace is removed from the user's leg, thereby permitting the brace to be custom fit to the user's leg.

9. The method of claim 8 wherein the connecting step comprises:

connecting first and second rigid thigh bars to the thigh cuff at opposite sides of the thigh cuff;

connecting first and second rigid calf bars to the calf cuff at opposite sides of the calf cuff;

connecting a first hinge to the first thigh bar and the first calf bar; and connecting a second hinge to the second thigh bar and the second calf bar;

wherein the support devices can be mounted to any of the thigh bars or calf bars.

10. The method of claim 8 wherein the pliable pad that deforms and hardens while remaining resilient comprises an open-celled foam impregnated with a water-curable prepolymer resin system enclosed in a sleeve, and wherein the step of permitting the pad to cure after a predetermined time comprises exposing the resin to water to cure the resin and maintain the shape of the user's leg.

11. The orthotic knee brace of claim 1 wherein the pliable pad that deforms and hardens while remaining resilient is the calf cuff pad.

12. The orthotic knee brace of claim 1 wherein both the thigh cuff pad and the calf cuff pad are pliable pads that deform and harden while remaining resilient.

13. An orthotic knee brace for providing support to the leg of a user, wherein the brace can be custom fit to the user's leg without requiring any separate casting or leg measuring steps other than to initially select the general size of the brace, the brace comprising:

a thigh cuff for fitting around the user's thigh;

a calf cuff for fitting around the user's calf;

means for hingably connecting the thigh cuff to the calf cuff;

means for providing support to at least a portion of the leg; and a pad removably disposed on the interior surface of both the thigh cuff and the calf cuff which contacts the user's leg, wherein at least one of the pads is pliable when placed around the user's leg and then deforms to conform to the shape of the user's leg, and after a predetermined time hardens while remaining resilient to maintain permanently the shape of the user's leg even after the brace is removed from the user's leg, thereby permitting the brace to be custom fit to the user's leg.

* * * * *

UNITED STATES PATENT AND TRADEMARK OFFICE
CERTIFICATE OF CORRECTION

PATENT NO. : 5,042,464
DATED : August 27, 1991
INVENTOR(S) : Edward P. Skwor, Timothy C. Sandvig and Franklin C. Lange It is certified that error appears in the above-identified patent and that said Letters Patent is hereby corrected as shown below:

Col. 1, line 12, "4,9068,542" should read --4,968,542--.

Col. 8, line 1, "mon" should read --on--.

Signed and Sealed this

Seventeenth Day of August, 1993

Attest:

BRUCE LEHMAN

*Attesting Officer*  *Commissioner of Patents and Trademarks*